(12) United States Patent
Min (10) Patent No.: US 12,296,081 B2
(45) Date of Patent: May 13, 2025

(54) PLASMAPHERESIS METHODS

(71) Applicant: Fenwal, Inc., Lake Zurich, IL (US)

(72) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 652 days.

(21) Appl. No.: 17/044,635

(22) PCT Filed: Apr. 3, 2019

(86) PCT No.: PCT/US2019/025572
§ 371 (c)(1),
(2) Date: Oct. 1, 2020

(87) PCT Pub. No.: WO2019/195414
PCT Pub. Date: Oct. 10, 2019

(65) Prior Publication Data
US 2021/0100943 A1    Apr. 8, 2021

Related U.S. Application Data

(60) Provisional application No. 62/652,211, filed on Apr. 3, 2018.

(51) Int. Cl.
*A61M 1/34*    (2006.01)
*A61M 1/26*    (2006.01)
(Continued)

(52) U.S. Cl.
CPC .......... *A61M 1/3496* (2013.01); *A61M 1/262* (2014.02); *A61M 1/3672* (2013.01);
(Continued)

(58) Field of Classification Search
CPC .. A61M 1/262; A61M 1/3496; A61M 1/3672; A61M 1/382; A61M 2205/3306; A61M 2230/20
See application file for complete search history.

(56) References Cited

U.S. PATENT DOCUMENTS 5,135,667 A  *  8/1992  Schoendorfer ....... A61M 1/302
                                                  210/257.2
2003/0062318 A1*  4/2003  Brown .................... B04B 13/00
                                                  210/512.1
(Continued)

FOREIGN PATENT DOCUMENTS

EP    1128887 A1    9/2001
EP    2392369 A1    12/2011
(Continued)

OTHER PUBLICATIONS

Supplemental European Search Report and European search Opinion issued Feb. 25, 2022 for European Application No. 19781341.3.
(Continued)

*Primary Examiner* — John Kim
(74) *Attorney, Agent, or Firm* — Cook Alex Ltd.

(57) ABSTRACT

Methods and systems for the automated collection of plasma from a donor are disclosed. The methods and systems deliver anticoagulant to whole blood and/or to selected and separated components at selected times to provide a sufficient amount of anticoagulant to the selected components to prevent coagulation and/or flocculation. The methods and systems limit the amount of anticoagulant returned to the donor and maximize the amount of collected plasma. Methods and systems for maximize the collection of IgG based on a measured level of total plasma protein are also disclosed.

13 Claims, 6 Drawing Sheets

(51) Int. Cl.
    *A61M 1/36*     (2006.01)
    *A61M 1/38*     (2006.01)
(52) U.S. Cl.
    CPC ..... *A61M 1/382* (2013.01); *A61M 2205/3306* (2013.01); *A61M 2230/20* (2013.01)

(56) References Cited

U.S. PATENT DOCUMENTS

| | | |
|---|---|---|
| 2005/0196393 A1 | 9/2005 | Shanbrom |
| 2014/0100507 A1 | 4/2014 | Flexman |
| 2014/0356851 A1* | 12/2014 | Pages ................... A61M 1/288 422/44 |
| 2016/0089486 A1 | 3/2016 | Patel et al. |
| 2017/0157307 A1* | 6/2017 | Brown ................ H05K 999/99 |

FOREIGN PATENT DOCUMENTS

| | | |
|---|---|---|
| EP | 3166659 A1 | 5/2017 |
| WO | 2015099826 A1 | 7/2015 |

OTHER PUBLICATIONS

Partial European Search Report and Provisional Opinion issued Nov. 24, 2021 for European Application No. 19781341.3.
International Search Report and Written Opinion issued Aug. 7, 2019 for International Application No. PCT/US2019/025572.
International Preliminary Report on Patentability Chapter I issued Oct. 6, 2020 for International Application No. PCT/US2019/025572.

* cited by examiner

PLASMAPHERESIS METHODS

CROSS-REFERENCE TO RELATED APPLICATIONS

This application is the U.S. National Stage Application of PCT Application No. PCT/US2019/025572, filed Apr. 3, 2019, which claims the benefit of and priority to U.S. Provisional Patent Application Ser. No. 62/652,211, filed on Apr. 3, 2018 the contents of which are incorporated herein by reference.

FIELD OF THE DISCLOSURE

The present disclosure is directed to plasmapheresis methods generally. More particularly, the present disclosure is directed to methods of collecting plasma with selective addition of anticoagulant to the collected whole blood and/or to the products collected during plasmapheresis. In another aspect, the present disclosure is directed to methods for determining the level of IgG in a donor and to maximizing the amount of IgG collected from plasmapheresis.

BACKGROUND

Plasmapheresis is an apheresis procedure in which whole blood is withdrawn from a donor, the plasma is separated from the cellular blood components (red blood cells, platelets and leukocytes) and collected, and the cellular blood components are returned to the donor. The separation of the plasma from the cellular components is typically accomplished in an automated procedure by centrifugation or membrane filtration.

In automated plasmapheresis, whole blood is drawn from the donor, mixed at a specified ratio with anticoagulant ("AC"), and then separated into anticoagulated plasma and red blood cells and other cellular components. The red blood cells and other cellular components are returned to the donor, and the anticoagulated plasma is collected into a container for later transfusion or further processing. The anticoagulated plasma is a mixture of (raw) plasma from the donor and anticoagulant, where the relative proportion of the two components depends on the donor blood hematocrit and the ratio at which the AC is combined with the donor's whole blood. The more anticoagulant that is combined with the whole blood, the more anticoagulant is present in the separated plasma and, as a result, less of the useful plasma is collected.

Plasma is often collected to serve as a source material ("source plasma") for further processing and source plasma collected from multiple donors is often combined or pooled together for this purpose. Plasma is commonly collected for its proteins, of which Immunoglobulin G, or IgG, is among the most valuable proteins as it has many medical applications. The overall demand of IgG is increasing annually. Thus, it would be desirable to collect as much plasma as possible in order to obtain as much IgG as possible.

The desire to collect as much plasma as possible and limit the amount of anticoagulant in the plasma must however be balanced against (i) the need for other blood components such as red blood cells to be sufficiently anticoagulated and (ii) the plasma itself to be sufficiently anticoagulated and avoid flocculation. Thus, it would be desirable to tailor the addition of anticoagulant to the withdrawn whole blood and/or the separated components as needed and when needed instead of relying on a single addition of anticoagulant to the whole blood at the beginning of a procedure based on traditional whole blood:AC ratios and citrate content of the anticoagulant.

With regard to maximizing the collection of plasma protein and IgG, in particular, it would be desirable to determine the level of total protein content in a donor in order to estimate the level of IgG in the donor, and collect an amount of plasma from the donor commensurate with the level of IgG of the donor.

SUMMARY

In one aspect, this disclosure is directed to a method of collecting plasma from anticoagulated whole blood having a reduced volume of anticoagulant including: withdrawing whole blood from a donor; combining the whole blood with a reduced volume of anticoagulant having a selected citrate content; separating the anticoagulated blood into plasma and red cells; collecting the separated plasma in a plasma collection container; and, if necessary adjusting the amount of anticoagulant in the plasma collection container.

In another aspect, this disclosure is directed to an automated plasmapheresis system including a reusable hardware component and a disposable fluid circuit mounted on the hardware component. The disposable fluid circuit includes a donor line terminating in a venipuncture needle for withdrawing whole blood from a donor. The fluid circuit also includes a separator for separating whole blood into a plasma fraction and a concentrated cell fraction, the separator having an input having a blood line integrally connected thereto for transporting whole blood from a donor to the separator. The separator also includes a plasma output port integrally connected to a plasma collection container by a plasma line, and a concentrated cell outlet port integrally connected to a reservoir for receiving concentrated cells prior to reinfusion to the donor. The circuit may further include an anticoagulant line integrally connected to the blood line and configured to be connected to a source of anticoagulant for transporting anticoagulant to the donor line.

The system will include a reusable hardware component further including a plurality of pumps for delivering anticoagulant to the whole blood, for delivering anticoagulated whole blood to the separator during the collection phase and for returning concentrated cellular components to the donor and for delivering concentrated cellular components from the separator to the reservoir. The hardware component also includes a programmable controller configured to direct the addition of selected amounts of anticoagulant to one or both of the plasma collection container and reservoir.

In a further aspect, this disclosure is directed to a method for determining the level of IgG in a donor and maximizing the collection of IgG from a donor including: a) measuring the total plasma protein level in a donor; b) estimating the amount of IgG based on the measured total plasma protein level; c) collecting a selected amount of plasma from the donor based on the estimated value of IgG.

DETAILED DESCRIPTION OF THE EMBODIMENTS

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

In the context of the present application, plasmapheresis is performed on an automated system comprising a hardware component, generally designated 10, and a disposable set, generally designated 12 (FIG. 3), to collect plasma to be processed as source plasma. With reference to FIGS. 1-5, and as described in greater detail below, the disposable fluid circuit 12 consists of an integrally connected separator, containers, and tubing to transport blood and solutions within a sterile fluid pathway.

Figure 2:
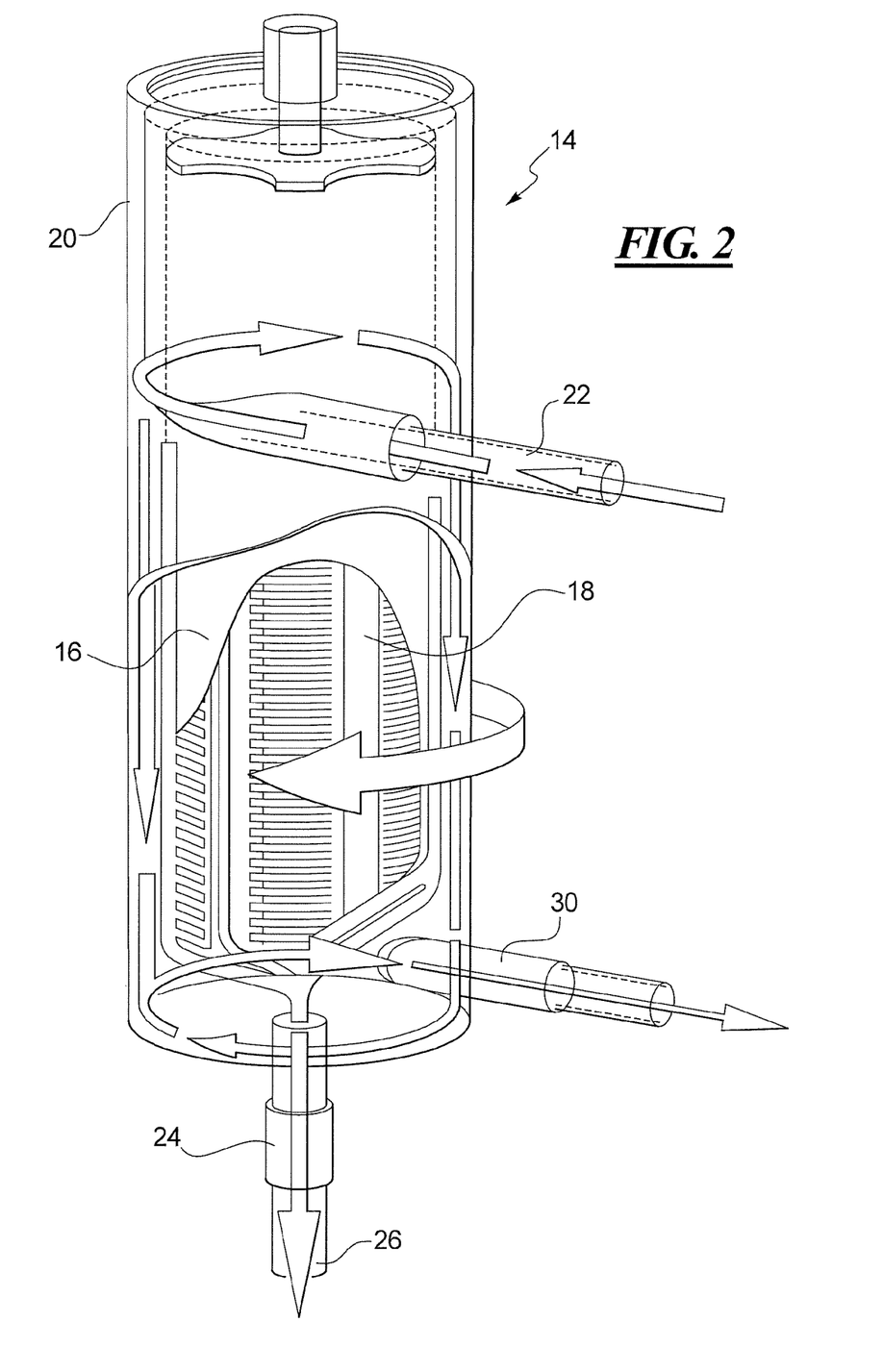
FIG. 2 is a perspective view of a spinning membrane separator of the type incorporated in a disposable set, with portions broken away to show detail, usable with the plasmapheresis system of FIG. 1.

The separator 14, best seen in FIG. 2, has a spinning membrane filter 16 mounted to a rotor 18 for rotation within a housing 20 to separate blood into components. A detailed description of a spinning membrane separator may be found in U.S. Pat. No. 5,194,145 to Schoendorfer, which is incorporated herein by reference. As can be appreciated, in a different system, separation of the whole blood may be accomplished by centrifugation. See, e.g. U.S. Pat. No. 5,360,542 to Williamson et al.

Figure 3:
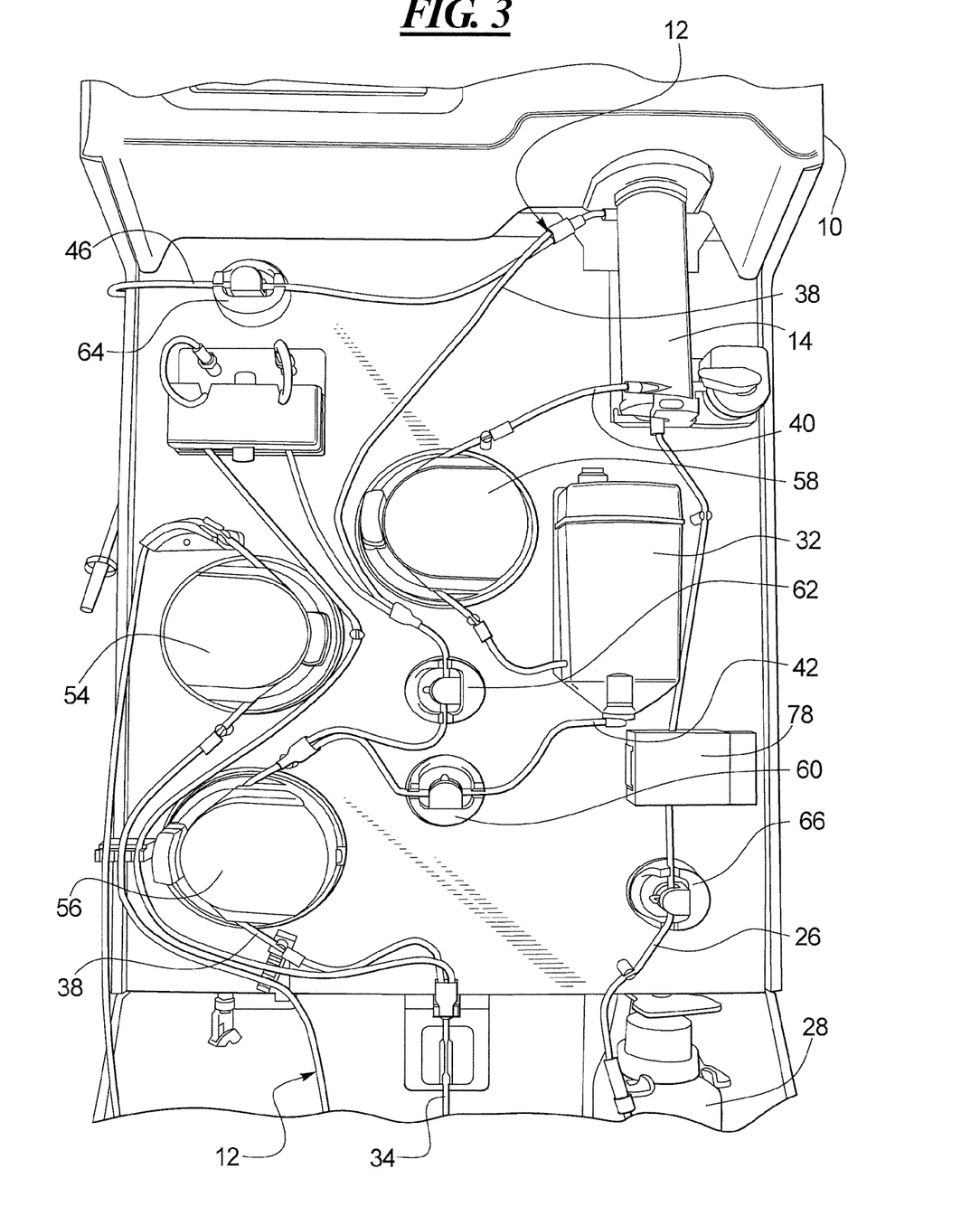
FIG. 3 is a perspective view of the front panel of the plasmapheresis system of FIG. 1 showing the components of the disposable set that are mounted thereto.
Figure 4:
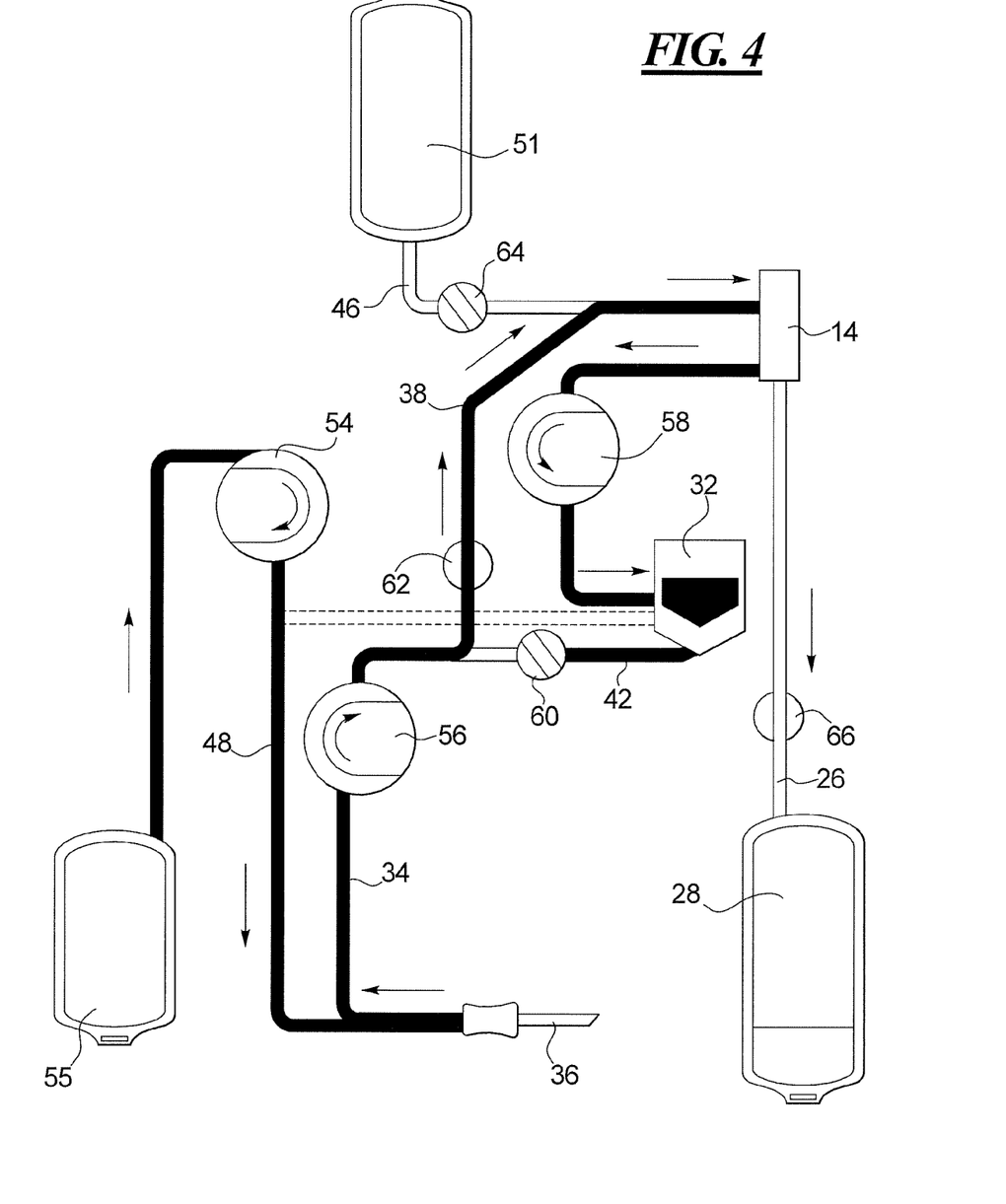
FIG. 4 is a schematic view showing operation of the plasmapheresis system in the collection phase.
Figure 5:
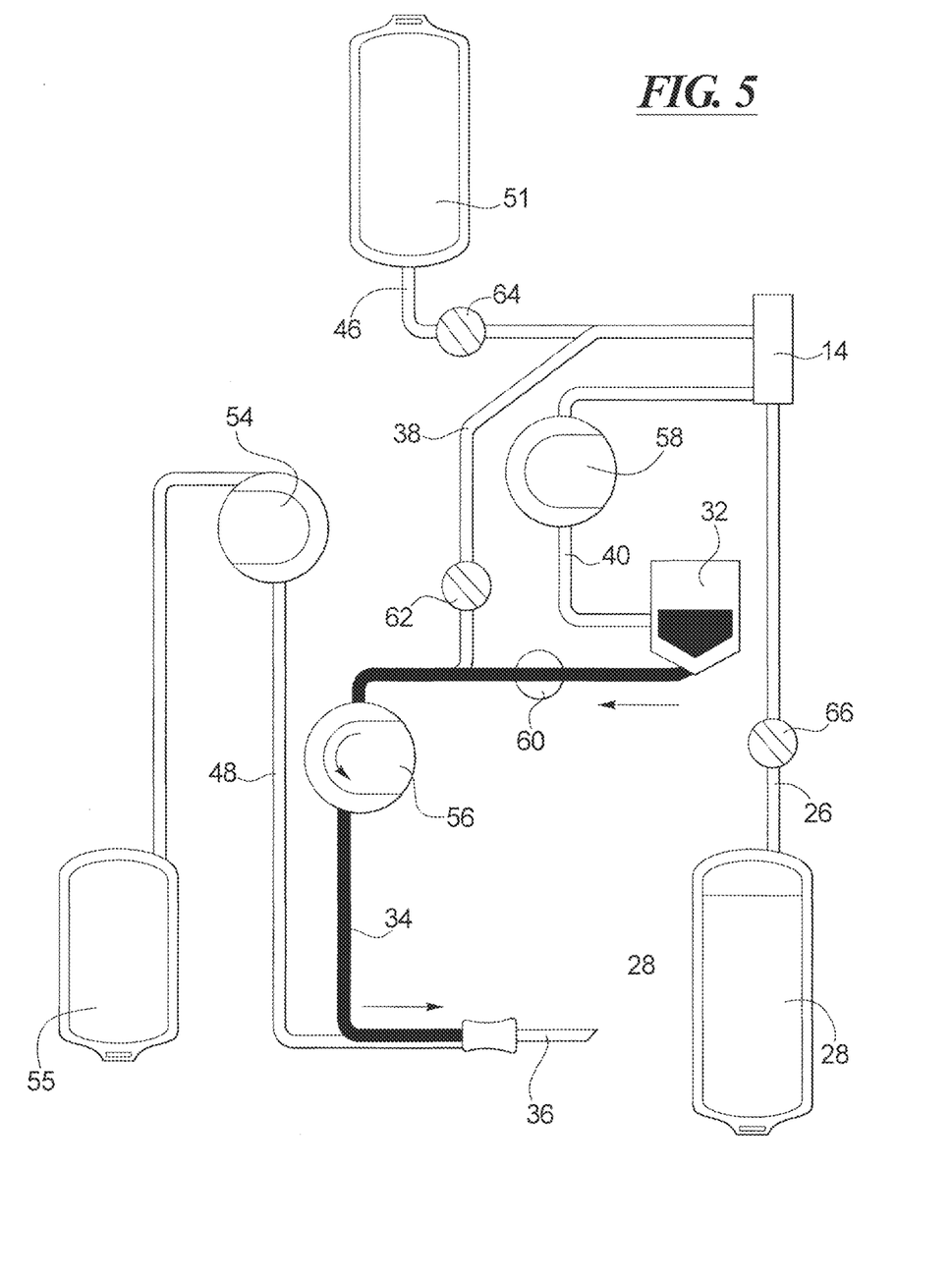
FIG. 5 is a schematic view showing operation of the plasmapheresis system in the reinfusion phase.

During plasmapheresis, anticoagulated whole blood enters the separator 14 through a whole blood input port 22. The plasma is separated by the spinning membrane filter and then passes out of a plasma output port 24, through a plasma line 26, and into a plasma collection container 28 (FIGS. 3-5). Concentrated cells are pumped out of a concentrated cell output port 30 into a reservoir 32, where the cells remain until reinfusion to the donor.

The disposable set 12 also includes tubing lines for introducing whole blood from the donor into the system during collection and returning concentrated cells to the donor during reinfusion (donor line 34, which terminates in the venipuncture needle 36), and for transporting anticoagulated whole blood to the separator (blood line 38), concentrated cells into the reservoir (cell line 40), concentrated cells from the reservoir to the donor line (reinfusion line 42), plasma into the plasma collection container (plasma line 26), saline (saline line 46), and anticoagulant (AC line 48).

The hardware component 10 includes a programmable controller 50 and, preferably, touch screen 52 with a graphical user interface ("GUI") through which the operator controls the procedure. For example, the GUI permits entry of a donor ID, donor gender, donor height, donor weight, donor hematocrit/hemoglobin; a target saline infusion volume (if a saline protocol is selected), and a target plasma volume. In accordance with the methods and systems described herein, controller may also be programmed to direct the addition of anticoagulant to the incoming whole blood, to reservoir 32 and to the plasma collection container 28. This includes the amount of anticoagulant and the time points in the plasmapheresis procedure, as will be discussed below. The touch screen 52 also enables the operator to gather status information and handle error conditions.

Typically, three peristaltic pumps are located on the front panel of the hardware component 10, including an AC pump 54, a blood pump 56, and a cell pump 58. The AC pump 54, under the direction of the controller, delivers anticoagulant solution (AC) from anticoagulant solution container (source) 55 at a controlled rate into the blood line 38 as whole blood enters the set from the donor. The blood pump 56 delivers anticoagulated whole blood to the separator during the collection phase of the procedure and returns concentrated cellular components and, if desired, replacement fluid to the donor during the reinfusion phase of the procedure. The cell pump 58 delivers concentrated cellular components from the separator 14 to reservoir 32 during the collection phase.

The front panel may also include clamps into which the disposable set 12 is installed, including a reinfusion clamp 60, a blood clamp 62, a saline clamp 64, and a plasma clamp 66. The reinfusion clamp 60 closes to block the reinfusion line (42) during the collection phase (FIG. 4) and is open during the reinfusion phase (FIG. 5) to allow the blood pump to reinfuse the concentrated cellular components from the reservoir 32 to the donor. The blood clamp 62 opens during the collection phase to allow anticoagulated whole blood to be pumped to the separator 14 and closes during the reinfusion phase to block the blood line 38. The saline clamp 64 closes to block the saline line 46 attached to saline source 51 during the collection phase and during reinfusion of the separated cellular components. If saline is to be used as a replacement fluid, the saline clamp 64 opens during the reinfusion phase. The plasma clamp 66 opens during the collection phase to allow plasma to flow into the plasma collection container 28 and closes during the reinfusion phase.

The hardware component 10 includes weigh scales to monitor the current plasma collection volume (scale 68), the AC solution volume (scale 70), and the concentrated cellular content volume (scale 72). The system also includes various sensors and detectors, including a venous pressure sensor 74, a separator pressure sensor 76, optical blood detectors 78, and an air detector 80.

The donor is connected to the system throughout the procedure. As illustrated, the disposable set 12 includes a single venipuncture needle 36, through which whole blood is drawn from the donor in a collection phase (FIG. 4) and concentrated cells are returned to the donor in a reinfusion stage (FIG. 5). During the collection phase, the whole blood is separated into plasma and concentrated cells. The disposable set includes a plasma collection container 28 for receipt of the separated plasma and a reservoir 32 for receipt of the concentrated cells. During the reinfusion phase, the concentrated cells from the reservoir 32 are reinfused to the donor through the venipuncture needle 36. Typically, plasmapheresis performed with a single venipuncture needle 36 involves multiple cycles of collection and reinfusion.

Returning to FIG. 4, during the collection phase, anticoagulant solution (AC) is pumped at a controlled rate from source 55 and mixed with whole blood as it enters the disposable set 12. The anticoagulated blood is pumped to the separator 14, where plasma is separated from the cellular components and directed to the plasma collection container 28.

The cellular components are pumped from the separator 14 to the reservoir 32. The collection phase stops when the reservoir 32 reaches an expected volume of concentrated cells or if the target plasma collection volume has been achieved.

The system automatically performs the plasmapheresis procedure until the specified volume of plasma product is collected, as determined by the weigh scale for monitoring the current plasma collection volume (scale 68). The weigh scale sends a signal to the controller when the desired volume is collected, and the controller then terminates the collection phase and initiates the final reinfusion phase, after which the donor is disconnected.

With reference to FIG. 5, during the reinfusion phase, the blood pump 56 reverses direction and pumps the concentrated cells from the reservoir 32 back to the donor through the apheresis needle 36. If a saline protocol was selected, by which saline is returned to the donor as a replacement fluid for the collected plasma, the final reinfusion phase is followed by saline infusion.

As noted above, incoming whole blood is combined with anticoagulant during whole blood withdrawal. A typical anticoagulant for plasmapheresis will include citrate such as sodium citrate solution, Acid Citrate Dextrose (ACD), solutions A or B, or citrate phosphate dextrose (CPD). The anticoagulant is combined with whole blood in a predetermined ratio wherein the anticoagulant includes a fixed percentage of citrate. Inasmuch as some of the separated components in a plasmapheresis procedure are reinfused back to the donor, the amount of anticoagulant and, more specifically, citrate must be controlled to avoid too much citrate being sent (returned) to the donor. Thus, typically a suitable ratio of whole blood to anticoagulant in a plasmapheresis procedure is approximately 16:1 or about 6% of the anticoagulated whole blood when the anticoagulant is sodium citrate solution. The ratio may be different where other anticoagulants, such ACD-A or ACD-B (which have slightly lower citrate content) are used.

The anticoagulant that is combined with the whole blood during the collection phase is carried over to the separated products such as the red blood cells and the plasma. The presence of anticoagulant in these products prevents coagulation of the red blood cells and flocculation of the plasma. However, as discussed above, the presence of anticoagulant in the collected plasma means that a portion of the collected plasma product is anticoagulant. For example, where anticoagulant (AC) is used at about 6% to the whole blood, the resulting plasma from this will include about 10% anticoagulant. Therefore, if one were to collect 500 ml of plasma, about 50 ml is actually AC and not plasma. It would be desirable to collect more plasma with a smaller percentage of AC in the plasma product.

Methods of Collecting Plasma with Selective Addition of AC

Example 1: In one embodiment, the initial volume of anticoagulant can be reduced while still providing the desired anticoagulating effect as would be achieved by a more traditional volume of anticoagulant.

As discussed above, a commonly used anticoagulant is 4% sodium citrate solution. In accordance with one embodiment of a method of the present disclosure, an anticoagulant with a higher citrate content may be used, allowing for a lower anticoagulant volume to conduct plasmapheresis. For example, if the anticoagulant solution includes 8% sodium citrate, then effectively half the volume of anticoagulant may be used. Thus, as described above, whereas 500 ml of plasma product anticoagulated with 4% sodium citrate will include 50 ml of anticoagulant, 500 ml of plasma product anticoagulated with 8% sodium citrate will require only half of the original anticoagulant volume and thereby will result in only 25 ml of anticoagulant in the final plasma product, yielding an additional 25 ml of plasma in the plasma collection bottle 28. Of course other multiples of the sodium citrate concentration may be used with commensurate reductions in the AC volume, such as a 5%, 6%, 7% sodium citrate and fractions thereof. Other anticoagulants such as ACD-A and ACD-B which have lower citrate concentrations (typically 2%-3%) may also be used in higher concentrations but with reduced volumes to allow for the collection of more plasma.

Example 2: In another embodiment, the amount of anticoagulant combined with the incoming whole blood can be reduced. While some anticoagulant is required to ensure that blood will not coagulate in the extracorporeal space in the disposable fluid circuit and that plasma will not flocculate in the plasma collection container 28, even without any anticoagulant, coagulation is not immediate and it will take some time before the blood will start to coagulate. Thus, even if the blood is minimally anticoagulated at the outset, the time for coagulation to begin will be delayed.

In the context of the system described herein and shown in the Figures, the time that the collected blood will spend in the space of the fluid circuit 12 between needle 36 and the separation device 14 that includes, for example, a spinning membrane ("spinner") and a reservoir is relatively short. For example, it takes less than approximately 20 seconds for whole blood to be processed in the spinner and for the red blood cells to be collected in the reservoir, and for plasma to be collected in the bottle.

Blood (red blood cells that have been separated from plasma in the separator) will typically reside in the reservoir for 2-3 minutes and sometimes more than 5 minutes before the contents is pumped back to the donor. If the red blood cells reside in the reservoir too long and a sufficient amount of anticoagulant is not added to the reservoir to anticoagulate the red blood cells, there is a risk that the blood in the reservoir will begin to coagulate.

In accordance with this embodiment of the method of the present disclosure, the system can be programmed to pump a selected volume of anticoagulant into reservoir 32 prior to the reinfusion cycle shown in FIG. 5. Anticoagulant may be added incrementally as red cells are added to reservoir 32, may be added at or near the end of the collection cycle, or preferably, may be added to reservoir 32 prior to the collection phase, such as during priming of the system For example, the system (controller) may be configured to add anticoagulant to reservoir 32 when the weight recorded by weigh scale 72 indicates that a predetermined amount of red cells have been collected, whether at the end of the procedure or before each collection cycle. In this example, addition of anticoagulant may occur between a collection cycle and a reinfusion cycle, shown respectively in FIGS. 4 and 5. Anticoagulant pump 54 may be activated (and blood pump 56 deactivated) by the controller when a collection cycle has been completed. Alternatively, disposable fluid circuit may include an additional line branching from AC line 48 (shown in broken lines in FIG. 4) and separately communicating with reservoir 32 thereby allowing delivery of anticoagulant to reservoir 32 continuously while separating the blood in separation device 14.

In accordance with the Example 2 described above, excess and unnecessary anticoagulant in the plasma product can be avoided by (i) combining less anticoagulant with the incoming whole blood and (ii) selectively adding anticoagulant to the reservoir holding the red blood cells or otherwise combining the returning red blood cells with anticoagulant (such as by introducing anticoagulant into line 34 during the reinfusion cycle.)

In a further alternative embodiment, AC may be added to reservoir 32 prior to the collection phase and, for example, when priming fluid circuit 12. In this embodiment, and prior to the collection phase, a volume of whole blood may be withdrawn from a donor and combined with a selected ratio of whole blood to anticoagulant. The ratio of whole blood:anticoagulant may include a greater amount of anticoagulant such as 8:1. The anticoagulated whole blood is pumped through the circuit 12 by action of blood pump 56 and AC pump 54 under the direction of the controller to arrive at the desired whole blood:AC ration (for example, 8:1). With plasma clamp 66 closed and the separator 14 not spinning, the anticoagulated whole blood is pumped from separator 14 by action of cell pump 58 under the direction of the controller to reservoir 32. Alternatively, a similar result may be achieved by delivering the anticoagulated whole blood directly to reservoir 32. In this alternative, clamp 62 may be closed, clamp 60 opened and anticoagulated whole blood is delivered to reservoir 32 prior to the collection phase. In any event, the anticoagulated whole blood in a WB:AC ratio of approximately 8:1 provides anticoagulant to reservoir 32, allowing for a different ratio of WB:AC to be used for the collection phase, as described below.

During the collection phase, controller may direct pump 54 and 56 to deliver a different ratio of whole blood:AC than was used during the "priming" action described above. For example, a WB:AC ratio with less AC may be used. For example, a WB:AC ratio of 32:1 may be used during the initial draw (after prime) of whole blood from donor. The anticoagulant previously introduced and now residing in reservoir 32 provides a sufficient amount of anticoagulant to the red blood cells that will be collected in the reservoir. On the other hand, the lower amount of anticoagulant in the post-prime, whole blood draw allows for more plasma to be collected in plasma collection container 28 while still providing sufficient AC to reduce the risk of flocculation. Priming, as described above, will be repeated before each successive collection phase.

Example 3: As described above, having less anticoagulant will allow for the collection of more plasma in plasma collection container 28. Of course, too little anticoagulant may result in flocculation in the plasma. On the other hand, adding a volume of anticoagulant will negate the purpose of collecting more plasma in a given container volume within applicable government regulations relative to limits on collected plasma volume.

Thus, in accordance with another embodiment of a plasmapheresis method, sodium citrate may be added to the plasma in powder form before or even after the procedure. Powder form anticoagulant will not increase the volume significantly and will anticoagulate the plasma properly. The powder form AC can be made into and supplied as a tablet for convenient handling. In one embodiment, the amount of powder added is sufficient to provide citrate content comparable to citrate content in liquid anticoagulant (e.g., 4% citrate). In one embodiment, 1-2 grams of sodium citrate powder may be added to a collected plasma volume.

The tablet can be placed in the bottle at the manufacturing plant, or placed in plasma collection container 28 by the bottle by the operator prior to initiating the plasmapheresis procedure. Alternatively the tablet can be added by the operator after the procedure is completed.

It will be appreciated that the methods in the Examples described above may be used alone or in conjunction with one another. The methods of Examples 2 and 3 wherein (i) the amount of anticoagulant combined with whole blood is adjusted during "priming" and in the post-prime whole blood withdrawal and (ii) an amount of anticoagulant is added to the plasma in the powdered form can be combined. Similarly, the methods of Examples 2 and/or 3 can be used together with the adjustment of citrate concentration and reduced volume method described in Example 1.

Methods for Collecting More IgG from Plasmapheresis

As discussed above, one reason for collecting plasma through plasmapheresis is to collect plasma protein which is typically fractionated from large pools of plasma. One of the most important proteins is the Immunoglobulin G, IgG. IgG is a valuable protein as it has many medical applications. The overall demand of IgG is increasing annually.

Currently plasma is collected from donors without knowing the IgG concentration of the donor. A plasma center can only collect more plasma in the hope that more IgG will be obtained. Measuring IgG content from a donor is a very tedious and expensive task for the plasma center.

Figure 6:
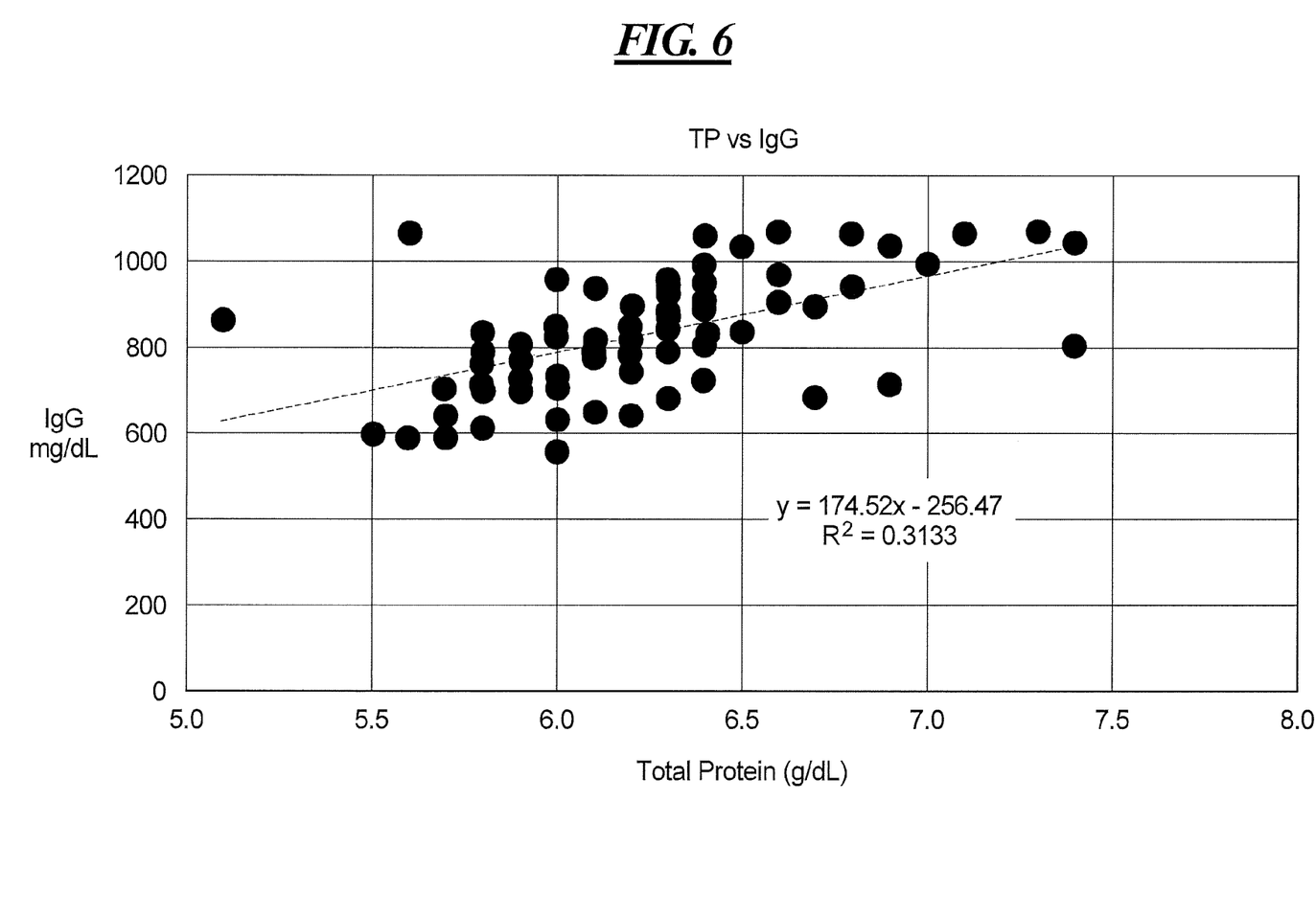
FIG. 6 is a graph showing the correlation of total protein and IgG.

There is a correlation between total protein and IgG. FIG. 6 shows experimental results from healthy volunteers which demonstrate that, in general, higher total protein level translates into higher IgG level. Accordingly, by screening donors who have more IgG and collect plasma from such donors, a higher yield of IgG will be achieved.

Although laboratory testing of total protein may be more accurate, there is a different and simpler way to assay the level of the total protein is provided. Here the preferred embodiment is using refractometer. A refractometer provides an optical measurement of the plasma estimating the protein level, since different levels of protein will make the refraction of the plasma different.

At the point of donor interview, one can use the refractometer to estimate the total protein level. From the table of FIG. 6, an estimate of the IgG level can be obtained and a suitable donation strategy can be established. Based on such estimates, the system may be programmed to collect a maximum and safe amount of plasma that will yield a maximum amount of IgG. More particularly the controller may be configured to collect a volume of plasma (within regulatory requirements) that maximizes IgG yield from a screened donor.

IgG levels vary widely from donor to donor. Based on experimental data, a lower value can as low as 600 mg/dL and the high value can be almost twice as high. Encouraging high IgG level donors to donate plasma will improve IgG yield in fractionation.

Figure 1:
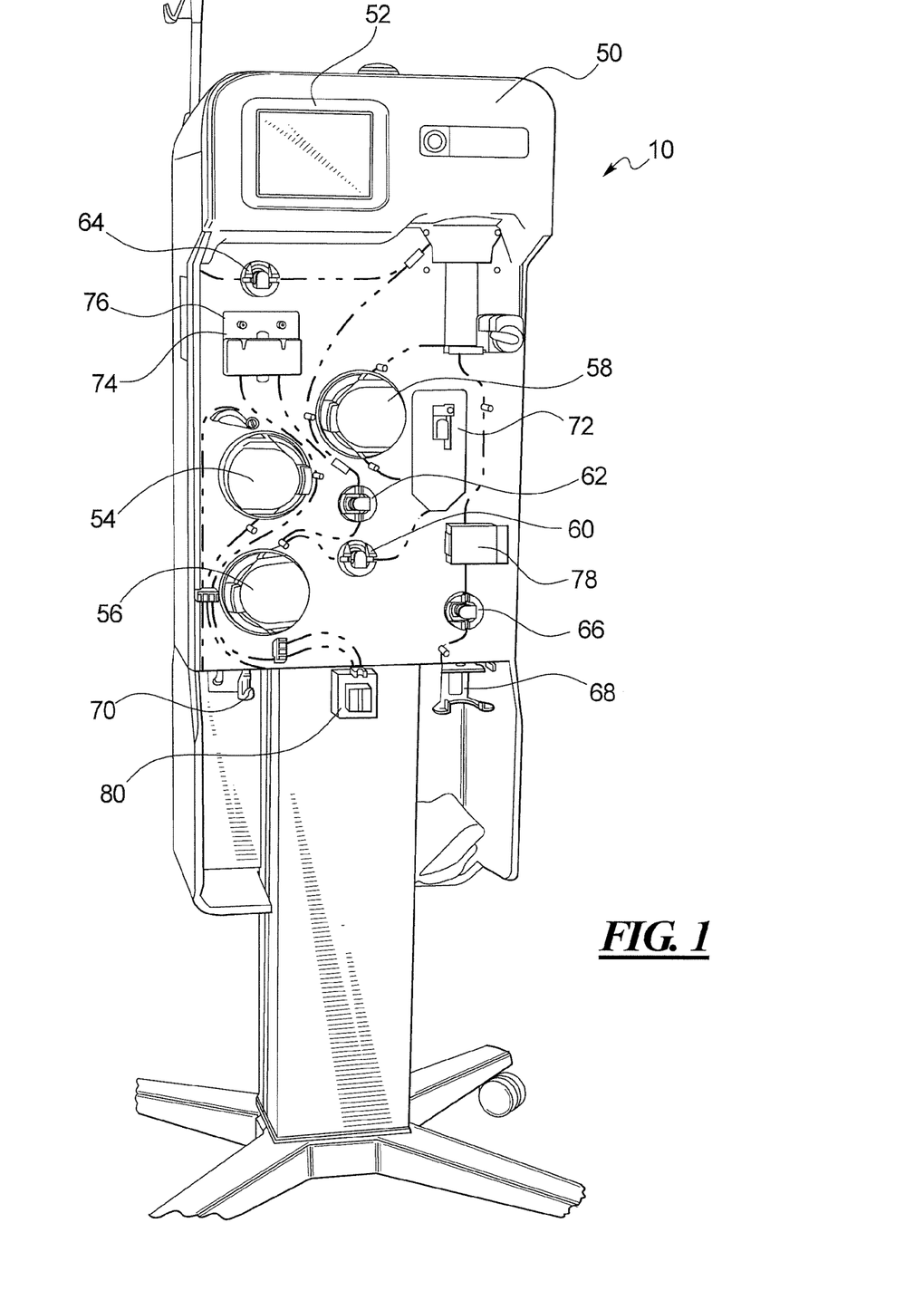
FIG. 1 is a perspective view of an exemplary plasmapheresis instrument suitable for use in the system and method of the present disclosure.

Optionally, determining a donor's plasma protein level may also be carried out during the plasmapheresis procedure in lieu of or in addition to an initial screening. As shown in FIG. 1, device 10 may be equipped with one or more optical sensors. One such sensor may be a refractometer 78 that receives plasma line 26. Refractometer 78 measures the level of plasma protein in the collected plasma product and the controller 50 calculates the IgG level in the donor. Based on the determined level of IgG of the donor, the system, under the direction of controller can adjust certain collection parameters such as duration of the procedure, the number of collection/reinfusion cycles to optimize and tailor the plasmapheresis procedure to the particular donor.

OTHER EXAMPLES

Aspects of the present subject matter described above may be beneficial alone or in combination with one or more other Aspects, as described below.

Aspect 1. A method of collecting plasma from anticoagulated whole blood having a reduced volume of anticoagulant including: withdrawing whole blood from a donor; combining the whole blood with a reduced volume of anticoagulant having a selected citrate content; separating the anticoagulated blood into plasma and red cells; collecting the separated plasma in a plasma collection container; and optionally adjusting the amount of anticoagulant in the plasma collection container.

Aspect 2. The method of Aspect 1 including returning the separated red blood cells to the donor.

Aspect 3. The method of Aspect 1 wherein the citrate content of the anticoagulant is greater than 4%.

Aspect 4. The method of Aspect 3 wherein the citrate content is greater than 4% and the ratio of whole blood to anticoagulant is 32:1.

Aspect 5. The method of Aspect 1 further including adjusting the amount of anticoagulant in the plasma collected in the plasma container by adding an amount of anticoagulant to the plasma collection container.

Aspect 6. The method of Aspect 5 including adding the anticoagulant to the plasma container after collecting the plasma in the plasma container.

Aspect 7. The method of Aspect 5 including adding the anticoagulant to the plasma container before collecting the plasma in the plasma container.

Aspect 8. The method of Aspect 7 including adding the anticoagulant to the plasma container in powder form.

Aspect 9. The method of Aspect 2 including collecting separated red blood cells in a reservoir prior to returning the red blood cells to the donor.

Aspect 10. The method of Aspect 9 including adding an amount of anticoagulant to the reservoir prior to returning the red blood cells to the donor.

Aspect 11. The method of Aspect 10 including adding the anticoagulant to the reservoir prior to introducing separated red blood cells into the reservoir.

Aspect 12. The method of any one of Aspects 9 through 11 including adjusting the amount of anticoagulant in the plasma collected in the plasma container by adding an amount of anticoagulant to the plasma collection container.

Aspect 13. The method of Aspect 12 including adding the anticoagulant to the plasma container before collecting the plasma in the plasma container.

Aspect 14. The method of Aspect 13 including adding the anticoagulant to the plasma container in powder form.

Aspect 15. An automated plasmapheresis system including a reusable hardware component and a disposable fluid circuit mounted on said hardware component: a) the disposable fluid circuit comprising (i) a donor line terminating in a venipuncture needle for withdrawing whole blood from a donor, (ii) a separator for separating whole blood into a plasma fraction and a concentrated cell fraction, the separator having an input having a blood line integrally connected thereto for transporting whole blood from a donor to the separator, a plasma output port integrally connected to a plasma collection container by a plasma line, and a concentrated cell outlet port integrally connected to a reservoir for receiving concentrated cells prior to reinfusion to the donor; and (iii) an anticoagulant line integrally connected to the blood line and configured to be connected to a source of anticoagulant for transporting anticoagulant to the donor line; and b) the reusable hardware component further comprising (i) a plurality of pumps for delivering anticoagulant to the whole blood, for delivering anticoagulated whole blood to the separator during the collection phase and for returning concentrated cellular components to the donor and for delivering concentrated cellular components from the separator to the reservoir and (ii) a programmable controller configured to direct the addition of selected amounts of anticoagulant to one or both of the plasma collection container and reservoir.

Aspect 16. The system of Aspect 15 wherein the programmable controller is configured to direct the addition of anticoagulant to the reservoir prior to receiving the concentrated cell fraction.

Aspect 17. The system of Aspect 15 wherein the plasma collection container includes a selected amount of anticoagulant prior to receiving plasma.

Aspect 18. The system of Aspect 17 wherein the anticoagulant is present in the plasma collection container in a powder form.

Aspect 19. The system of Aspect 17 wherein the anticoagulant is present in the plasma collection container in tablet form.

Aspect 20. A method for maximizing the collection of IgG from a donor including: a) measuring the total plasma protein level in a donor; b) estimating the amount of IgG based on the measured total plasma protein level; c) collecting a selected amount of plasma from the donor based on the estimated value of IgG.

Aspect 21. The method of Aspect 20 including measuring the total protein level in a donor with a refractometer.

Aspect 22. The method of Aspect 21 including measuring the total protein level prior to beginning a plasmapheresis procedure.

Aspect 23. The method of Aspect 21 including measuring the total protein level during a plasmapheresis procedure.

Aspect 24. The method of Aspect 21 including determining a donation strategy based on the estimating.

Aspect 25. The method of Aspect 21 wherein the measuring the total protein level is performed by a refractometer of an automated plasmapheresis system, the system comprising a reusable hardware component and a disposable fluid circuit mounted on the hardware component: a) the disposable fluid circuit comprising (i) a donor line terminating in a venipuncture needle for withdrawing whole blood from a donor, (ii) a separator for separating whole blood into a plasma fraction and a concentrated cell fraction, the separator having an input having a blood line integrally connected thereto for transporting whole blood from a donor to the separator, a plasma output port integrally connected to a plasma collection container by a plasma line, and a concentrated cell outlet port integrally connected to a reservoir for receiving concentrated cells prior to reinfusion to the donor; and (iii) an anticoagulant line integrally connected to the blood line and configured to be connected to a source of anticoagulant for transporting anticoagulant to the donor line; and b) the reusable hardware component further comprising (i) a plurality of pumps for delivering anticoagulant to the whole blood, for delivering anticoagulated whole blood to the separator during the collection phase and for returning concentrated cellular components to the donor and for delivering concentrated cellular component from the separator to the reservoir (ii) a refractometer for receiving the plasma line of the disposable fluid circuit and (iii) a programmable controller configured to direct or adjust the collection of plasma based on the measurement of the total protein level by said refractometer.

It will be understood that the embodiments described are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above-description, but is set forth in the following claims.

What is claimed is:

1. A method of collecting blood components from anticoagulated whole blood having a selected volume of anticoagulant comprising:
    a) withdrawing whole blood from a donor;
    b) combining said whole blood with a selected volume of anticoagulant having a citrate content of greater than 4%;
    c) separating said anticoagulated blood into plasma and red blood cells;
    d) collecting said separated plasma in a plasma collection container;
    e) collecting separated red blood cells in a reservoir;
    f) monitoring the amount of red blood cells collected in said reservoir; and
    g) introducing an amount of anticoagulant into said reservoir when a predetermined amount of red blood cells has been collected in said reservoir.

2. The method of claim 1 comprising returning said separated red blood cells to said donor.

3. The method of claim 1 wherein the citrate content of the anticoagulant is 8%.

4. The method of claim 3 comprising combining said whole blood with said anticoagulant in a ratio of whole blood to anticoagulant of approximately 32:1.

5. The method of claim 1 further comprising adjusting said amount of anticoagulant in the plasma collected in the plasma container by adding an amount of anticoagulant to said plasma collection container.

6. The method of claim 5 comprising adding anticoagulant to said plasma container after collecting said plasma in said plasma container.

7. The method of claim 5 comprising adding anticoagulant to said plasma container before collecting said plasma in said plasma container.

8. The method of claim 7 comprising adding said anticoagulant to said plasma container in powder form.

9. The method of claim 1 comprising adding an amount of anticoagulant to said reservoir prior to returning said red blood cells to said donor.

10. The method of claim 9 comprising adding said anticoagulant to said reservoir prior to introducing separated red blood cells into said reservoir.

11. The method of claim 1 comprising adjusting said amount of anticoagulant in the plasma collected in the plasma container by adding an amount of anticoagulant to said plasma collection container.

12. The method of claim 11 comprising adding said anticoagulant to said plasma container before collecting said plasma in said plasma container.

13. The method of claim 12 comprising adding said anticoagulant to said plasma container in powder form.

* * * * *